United States Patent
Weissgerber et al.

[11] Patent Number: 5,494,258
[45] Date of Patent: Feb. 27, 1996

[54] VALVE

[75] Inventors: Hans G. Weissgerber, Straubenhardt; Wolfgang Wilde, Karlsbad, both of Germany

[73] Assignee: Hewlett-Packard Company, Palo Alto, Calif.

[21] Appl. No.: 248,240

[22] Filed: May 24, 1994

[30] Foreign Application Priority Data

May 28, 1993 [DE] Germany .......................... 9308058 U

[51] Int. Cl.$^6$ ................................................. F16K 31/02
[52] U.S. Cl. ........................ 251/368; 251/82; 251/129.17
[58] Field of Search ........................ 251/368, 82, 129.17

[56] References Cited

U.S. PATENT DOCUMENTS

| | | | |
|---|---|---|---|
| 3,642,545 | 2/1972 | Pammer et al. ...................... | 148/187 |
| 3,874,635 | 4/1975 | Fletcher et al. ...................... | 251/333 |
| 4,139,469 | 2/1979 | Rainin et al. | |
| 4,734,187 | 3/1988 | Visentin et al. | |
| 4,832,075 | 5/1989 | Dubach . | |
| 4,862,907 | 9/1989 | Ledtje et al. ...................... | 137/1 |
| 5,002,662 | 3/1991 | Ledtje et al. | |
| 5,151,178 | 9/1992 | Nickerson et al. | |
| 5,271,427 | 12/1993 | Berchem ............................. | 137/375 |

FOREIGN PATENT DOCUMENTS

| | | |
|---|---|---|
| 0328696A1 | 8/1989 | European Pat. Off. . |
| 0328696 | 8/1989 | European Pat. Off. . |
| 2604166A1 | 8/1977 | Germany . |
| 2834146 | 2/1980 | Germany . |
| 86073 | 1/1920 | Switzerland . |
| 674559A5 | 6/1990 | Switzerland . |
| 1218228 | 1/1971 | United Kingdom . |
| 1516759 | 7/1978 | United Kingdom . |
| 1535441 | 12/1978 | United Kingdom . |
| WO92/21635 | 12/1992 | WIPO . |

*Primary Examiner*—A. Michael Chambers
*Attorney, Agent, or Firm*—Wolf, Greenfield & Sacks

[57] ABSTRACT

A valve for regulating the flow of a liquid, for example in liquid chromatography, comprises a valve seat and a valve ball which are made of electrically conductive ceramic or glass material. Due to the electric conductivity, electrostatic charging is avoided which would otherwise attract dirt particles and lead to contamination and leakage of the valve. The valve is chemically inert and is not corroded by the solvents typically used in analytical chemistry.

7 Claims, 1 Drawing Sheet

VALVE

The invention relates to a valve for regulating the flow of a liquid, with at least two sealing elements, for example a valve seat and a valve ball. Such valves are used, for example, in pumps for analytical measuring instruments such as liquid chromatographs.

BACKGROUND OF THE INVENTION

Liquid pumps in use with analytical measuring instruments require a high flow accuracy. In order to meet this requirement the pumps must be equipped with precision valves. Usually ball and seat type valves are used. Passive valves, wherein the valve ball is lifted by the flow of liquid, are known, for example, from U.S. Pat. No. 3,810,716 or from U.S. Pat. No. 4,139,469. The valve balls are often made of ruby and the seat of sapphire. Valves, wherein the ball and seat are composed of aluminum oxide ceramics ($Al_2O_3$), are also known. Such ceramic valves are described in U.S. Pat. No. 4,832,075 or in U.S. Pat. No. 4,862,907 or in U.S. Pat. No. 5,002,662. These ceramic valves produced by the die-pressing method have economic and other advantages over ruby/sapphire valves.

Both the ruby/sapphire and the $Al_2O_3$-ceramic/$Al_2O_3$-ceramic combinations have considerable advantages in use with a pump for high-pressure liquid chromatography. These advantages are: resistance to wear, chemical resistance to commonly used solvents, accuracy of form for good sealing properties, a high machining quality at economically efficient manufacturing costs. In high-pressure liquid chromatography it is possible, especially where ruby/sapphire valves are being used, that under the influence of acetonitrile and water a coating of organic substances forms on the valve material. As a result of this coating the ball will adhere to the seat and the surface of the seat will become contaminated. This problem can be reduced by using $Al_2O_3$ ceramics instead of ruby or sapphire.

Besides the mentioned passive valves, active valves may also be used in pumps for analytical measuring instruments, wherein the valve ball can be activated by a valve actuator. Such an active valve is known from EP-A-0 328 696. Active valves have the advantage that no flow reversal is required to close the valve. Further, movement of the valve elements is largely independent of external influences. Either ceramics or ruby/sapphire can be used as materials for the ball and seat.

The disadvantage of the valves as described above is their great tendency to become dirty. In particular in high-pressure liquid chromatography, it is impossible to avoid that smallest particles of dirt are deposited. These particles either originate from supply vessels, become detached from the feed system or are solids entrained in the solvent. These particles of dirt can build up on the valve. Once sufficient dirt has accumulated on the sealing surface the valve ceases to be tight and must be replaced.

SUMMARY OF THE INVENTION

It is thus an object of the invention to create a valve of the type mentioned above, wherein the sealing elements, for example the ball and seat in a ball valve, are prevented from becoming contaminated.

It is a further object of the invention to provide a valve which is chemically inert so that it is not corroded by the solvents typically used in analytical chemistry, and which has a long service life.

It is an additional object of the invention to provide a valve which can be manufactured with high precision in an easy way at a comparatively low price.

These and other objects of the invention are met by a valve as defined in the independent claims. According to an underlying principle of the invention, the sealing elements, such as a valve seat and a valve ball, comprise ceramic or glass material which is electrically conductive. The electric conductivity is achieved either by addition of substances to the usual ceramic or glass base material or by providing an electrically conductive coating on the ceramic or glass material.

The invention is based on the finding that the mentioned contamination of the prior art valves arises from the fact that the sealing elements, for example the valve ball and the valve seat, are electrostatically charged by fluid friction and thus cause electrostatic forces to act on the particles of dirt present in the liquid, whereby these particles are attracted and accumulate on the valve. The invention prevents electrostatic charging by selecting an electrically conductive ceramic or glass material for the sealing elements. The sealing elements therefore do not cause electrostatic forces to act on particles of dirt, with the result that these do not accumulate on the valve and the valve remains tight.

The contamination problem is therefore solved and at the same time the positive characteristics of a ceramic or glass valve as described above are retained. In particular, a valve, according to the invention has a longer service life than conventional valves.

A further advantage of the invention is that the sealing elements, especially the valve seat, can be manufactured more economically than is the case with valves made of sapphire. According to the an embodiment of invention using ceramics, powder is used as a starting material, which enables the basic shape of a seat to be directly sintered. That is to say, the powder (with a particle size in the micrometer range) is placed in a metal die which is roughly the negative of the finished part. This means that the cost of the subsequent grinding process is reduced considerably compared with the manufacture of a sapphire seat. In an economically advantageous way, 100 or more parts can be pressed and sintered at the same time in a metal die.

In an embodiment of the invention the electrically conductive ceramic material is composed of a mixture of aluminum oxide ($Al_2O_3$) and titanium carbide (TIC). The conductive ceramic material is preferably manufactured by sintering and subsequent further densification at high temperatures and under pressure. A valve according to the invention can, for example, be designed as an active valve with an actuator for activating a sealing element, for example the valve ball, or as a passive valve. In either case, the invention prevents particles of dirt from accumulating on the valve, which would result in loss of tightness.

BRIEF DESCRIPTION OF THE DRAWINGS

Subsequently, embodiments of the invention are explained in detail with reference to the drawings.

DETAILED DESCRIPTION OF THE INVENTION

Figure 1:
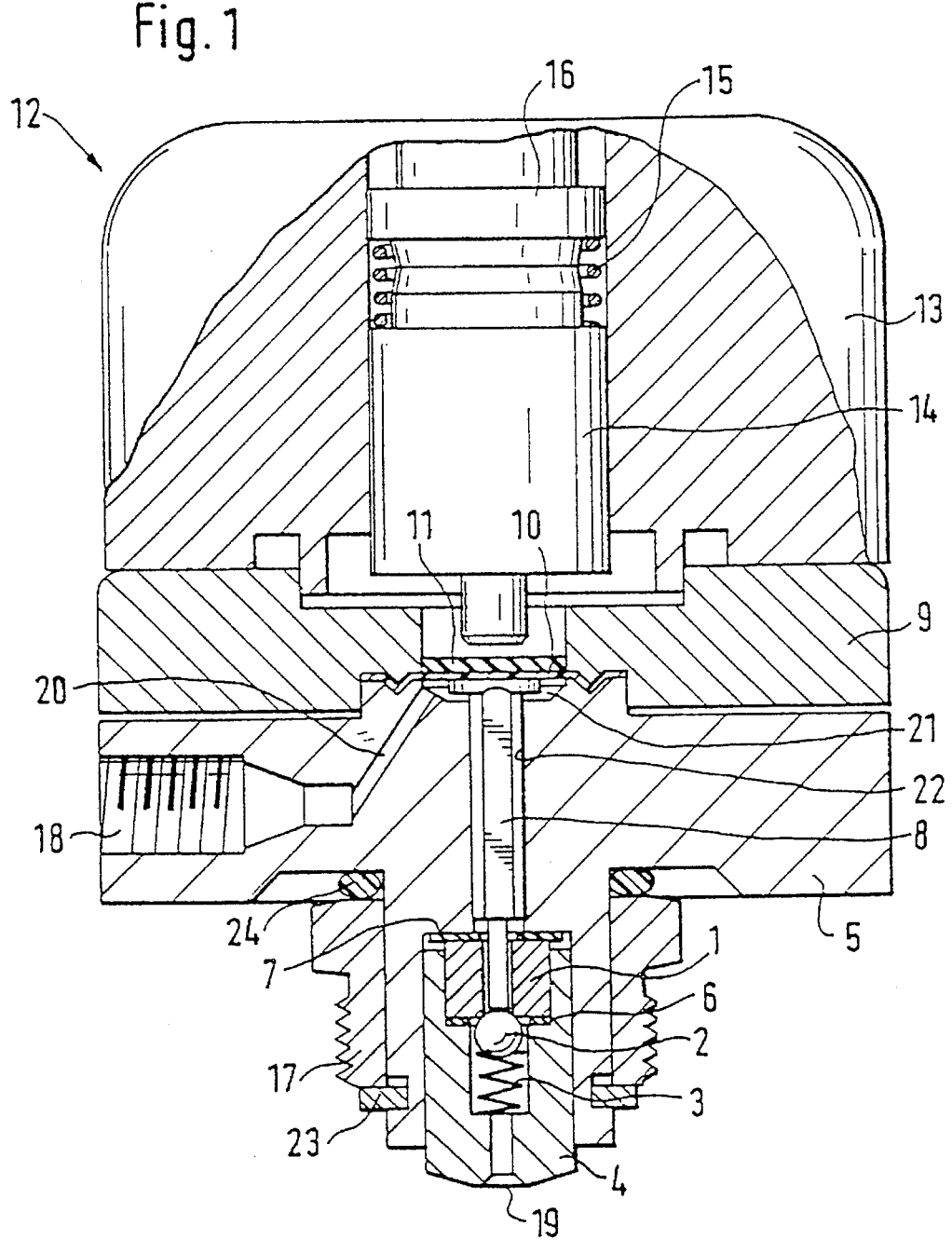
FIG. 1 shows a valve according to an embodiment of the invention in cross-section.

Referring to FIG. 1, the valve according to an embodiment of the invention comprises an inlet port 18 and an outlet port 19. The inlet port can, for example, be connected to a liquid supply vessel, by screwing a connecting tube on to the thread shown. The outlet port 19 can, for example, be connected to a pump. A preferred application for the valve according to the invention is in the field of high-pressure liquid chromatography where the inlet port 18 is connected to a vessel containing solvents or liquid samples and the outlet port 19 is connected to the inlet of a high-pressure pump.

Inside the valve liquid can flow from the inlet port 18 along the connecting channel 20 into the cavity 21 which is sealed on one side by a diaphragm 10. Liquid can flow from this cavity through a further connecting channel 22 and a ball valve (if open), which comprises a ball 2 and a seat 1, to the outlet port 19.

The valve ball 2 is held in place in the seat 1 by a preloaded spring 3. The valve seat 1 is clamped in position between an insert 4 and a valve body 5.

Sealing rings 6 and 7 are provided between the insert 4 and the seat 1 and between the valve body 5 and the seat 1. The insert 4, together with the seat 1 and the ball 2, the spring 3 and the sealing ring 6 are pressed into the valve body 5 so that the seat 1 is in contact with the sealing ring 7. Instead of the press fit as described above, the insert 4 and the valve body 5 could also be welded, cemented or screwed together.

In FIG. 1 the ball valve is shown in the closed position. The valve can be opened by means of an activating stem 8 which extends from the cavity 21 through the connecting channel 22 and the seat 1 to the ball 2. The activating stem is shown in detail in FIG. 2. As can be seen, the stem 8 consists of a head end 40, a middle section 41 and a tail end 42. The head end 40 is provided with a recess 43. This recess ensures that liquid can flow through the connecting channel 20 and the cavity 21 into the connecting channel 22, even if the stem 8 is pressed against the valve body 5. The part of the stem which extends into the connecting channel 22 is rectangular in cross-section and the longer side is somewhat smaller than the cross-section of the connecting channel 22 so that the stem can be moved inside the connecting channel. The activating stem 8 tapers towards its lower end and passes through the seat 1 until it touches the valve ball 2. The diameter of the tail end 42 has been chosen to permit liquid to flow between the stem and the internal wall of the seat.

The purpose of the screwed end 17 and the retaining ring 23 is to enable the valve to be flange-mounted on a pump head. The seal 24 produces a positive connection between the screwed end 17 and the valve body 5. As previously mentioned, the cavity 21 in which the head of the activating stem 8 is located is sealed by the diaphragm 10. The diaphragm is clamped in position in a V groove between an adapter plate 9 and the valve body 5. On the other side of the diaphragm 10 is a rubber disc 11 which serves as a cushion plate when the stem 8 is being actuated.

The stem 8 is actuated by a switching magnet 12, which is connected to the adapter plate 9. The switching magnet consists of a housing 13, an armature 14, a spring 15 and a limit stop 16. The coil for activating the switching magnet is located inside the housing 13. When the coil is activated, the armature 14 is pressed against the spring 15. Thus, no force is exerted on the stem 8, with the result that the spring 3 presses the valve ball 2 into the seat and the valve is closed. In order to open the valve the switching magnet is deactivated so that the armature 14 presses against the rubber disc 11. In this way the stem 8 is displaced and the ball 2 is lifted clear of the seat.

According to an important aspect of this embodiment of the invention the valve ball 2 and the valve seat 1 are composed of an electrically conductive ceramic material. An example of such conductive ceramic material is a mixture of aluminum oxide ($Al_2O_3$) and titanium carbide (TiC). In one embodiment the proportions are approximately 10% TiC and 90% $Al_2O_3$. This conductive ceramic material has an electrical resistivity of approx. $2.1 \cdot 10^{-3}$ Ohm.cm. This makes it possible to prevent the aforementioned contamination problem. In this particular embodiment (10% TiC and 90% $Al_2O_3$) the ceramic material has a density of 4.2 g/cm$^3$ and its crystallite size is less than 3 micrometers.

In order to produce the conductive ceramic material the components, in this example $Al_2O_3$ and TiC are sintered densely and further densified at high temperature while under pressure. The material thus obtained is then finished, in particular by grinding, to produce the ball and seat. This finishing process is comparable with the production of the ball and seat from sapphire and ruby respectively. As an alternative to the production process as described the ball and seat can also be sintered in approximately the desired form although the above mentioned further densification at high temperature while under pressure must also be used in this case.

Of course, other conductive ceramic materials besides $Al_2O_3$ and TiC can also be used. Other examples are SiC with free Si or SiC with TiB. The following general rule applies to electrical resistance: the smaller the electrical resistance the less the component will be electrically charged and accumulate dirt as a result of static electricity.

Figure 2:
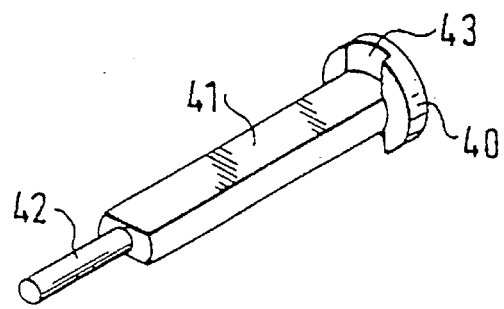
FIG. 2 is a perspective view of the activating stem as shown in FIG. 1.

In a further embodiment of the invention, the valve has substantially the same design as shown in FIGS. 1 and 2, but the valve ball and the valve seat are made of electrically conductive glass instead of electrically conductive ceramics. Such valves of electrically conductive glass have substantially the same advantages as those made of conductive ceramics (see above). An example for electrically conductive glass is the glass sold by the company Schott under the name "S 8900". The glass is doped with iron ions (Fe 2+ and Fe 3+ ions). As an alternative to the ball valve design, a design with a plate and a hole manufactured from conductive glass can be used. The use of glass material allows to apply alternative manufacturing processes, such as etching processes. Furthermore, smaller dimensions of the sealing components can be achieved with the glass technology.

According to a still further embodiment of the invention, the material for the valve ball and the valve seat is a substantially non-conductive ceramic or glass material which is covered at the surface by a layer of electrically conductive material. An example for such an electrically conductive material is gold. The gold layer is applied, for example, by a sputtering method. Further examples of materials used as a conductive surface layer are $SnO_2$ and $InSnO_2$; these are preferably applied on glass material. With the latter substances conductivities up to 20 Ohm/cm can be achieved.

The valve shown in FIG. 1 is an active valve wherein the valve ball is pushed out of the seat by a valve actuator. In an alternative active valve the valve seat could move and the valve ball remain static.

It is understood that the invention is not only for use in active valves but also in passive valves, in particular check valves wherein the ball is lifted by the flow of liquid. The use of ceramic or glass materials which are either conductive or covered with a conductive layer in such valves prevents particles of dirt from accumulating on the valve and impeding its operation. These check valves may be of the single seat or multiple seat type, i.e. provided with several ball/seat assemblies. Such a multiplicity of serially connected ball/seat assemblies can be arranged in a single housing or in separate housings, connected via a tube. Furthermore, ball/seat assemblies according to the invention could be connected in parallel. Such a parallel arrangement can be useful if the pressure drop across a single valve becomes too high.

It is also understood that the above mentioned arrangements of ball/seat assemblies of the invention, i.e., serial or parallel connection of several valves, is not limited to check valves, but can also be used with active valves.

The invention can be used to particular advantage in analytical instruments, especially those used in liquid chromatography. In this equipment accurate flow control and therefore the precise operation of the valves is very important for accuracy of measurement. However, it is also understood that the invention is not restricted to this field of application.

We claim:

1. Valve for regulating the flow of a liquid, for example in liquid chromatography, with at least two sealing elements, for example a valve seat (1) and a valve ball (2), characterized in that the sealing elements (1, 2) are made of electrically conductive ceramic material comprising a mixture of approximately 90% $Al_2O_3$ and 10% TiC.

2. Valve as in claim 1, wherein the electrically conductive ceramic material has a density of 4.2 g/cm$^3$ and a crystallite size of less than 3 micrometers.

3. Valve for regulating the flow of a liquid, for example in liquid chromatography, with at least two sealing elements, for example a valve seat (1) and a valve ball (2), characterized in that the sealing elements (1, 2) are made of electrically conductive ceramic material wherein the electrically conductive ceramic material is selected from the group consisting of:

(a) $Al_2O_3$ and TiC;

(b) SiC and free Si; and (c) SiC and TiB.

4. Valve for regulating the flow of a liquid, for example in liquid chromatography, with at least two sealing elements, for example a valve seat (1) and a valve ball (2), characterized in that the sealing elements (1, 2) are made of electrically conductive ceramic material wherein the electrically conductive material has an electrical resistivity of approximately $2.1 \times 10^{-3}$ Ohm.cm.

5. Valve for regulating the flow of a liquid, for example in liquid chromatography, with at least two sealing elements, for example a valve seat (1) and a valve ball (2), characterized in that the sealing elements (1, 2) are made of electrically conductive glass material wherein the glass material is doped with iron ions.

6. Valve for regulating the flow of a liquid, for example in liquid chromatography, with at least two sealing elements, for example a valve seat (1) and a valve ball (2), characterized in that the sealing elements (1, 2) are made of electrically conductive glass material wherein the glass material is covered with a conductive layer at its surface and the conductive layer is selected from the group consisting of $SnO_2$ and $InSnO_2$.

7. The valve according to the claims 1, 3, 4, 5, or 6, wherein the electrical resistivity of the valve is at most $2.1 \times 10^{-3}$ Ohm.cm.

* * * * *

UNITED STATES PATENT AND TRADEMARK OFFICE
CERTIFICATE OF CORRECTION

PATENT NO. : 5,494,258
DATED : February 27, 1996
INVENTOR(S) : Weissgerber et al.

It is certified that error appears in the above-indentified patent and that said Letters Patent is hereby corrected as shown below:

Col. 2, line 46. - delete "(TIC)" and substitute therefore -- (TiC) --.

Col. 4, line 5 - delete "(TIC)" and substitute therefore -- (TiC) --.

Signed and Sealed this

Twenty-eighth Day of May, 1996

*Attest:*

BRUCE LEHMAN

*Attesting Officer*   *Commissioner of Patents and Trademarks*